(12) United States Patent
Zhou et al.

(10) Patent No.: US 11,761,944 B2
(45) Date of Patent: Sep. 19, 2023

(54) EXPLORATION METHOD AND SYSTEM FOR PEGMATITE VEINS

(71) Applicant: Institute of Geology and Geophysics, Chinese Academy of Sciences, Beijing (CN)

(72) Inventors: Nannan Zhou, Beijing (CN); Guoqiang Xue, Beijing (CN); Shun Zhang, Beijing (CN); Xinhao Wei, Beijing (CN)

(73) Assignee: INSTITUTE OF GEOLOGY AND GEOPHYSICS, CHINESE ACADEMY OF SCIENCES, Beijing (CN)

( * ) Notice: Subject to any disclaimer, the term of this patent is extended or adjusted under 35 U.S.C. 154(b) by 0 days.

(21) Appl. No.: 17/991,056

(22) Filed: Nov. 21, 2022

(65) Prior Publication Data
US 2023/0168236 A1 Jun. 1, 2023

Related U.S. Application Data

(63) Continuation of application No. PCT/CN2022/074865, filed on Jan. 29, 2022.

(30) Foreign Application Priority Data

Dec. 1, 2021 (CN) .......................... 202111453224.4

(51) Int. Cl.
*G01V 3/08* (2006.01)
*G01N 33/24* (2006.01)
*G01V 3/38* (2006.01)
*G01N 27/04* (2006.01)

(52) U.S. Cl.
CPC ............. *G01N 33/24* (2013.01); *G01N 27/04* (2013.01); *G01V 3/088* (2013.01); *G01V 3/38* (2013.01)

(58) Field of Classification Search
CPC ........ G01N 33/24; G01N 27/04; G01V 3/088; G01V 3/38
See application file for complete search history.

(56) References Cited

FOREIGN PATENT DOCUMENTS

CN 101749013 A 12/2009
CN 107765314 A * 3/2018

* cited by examiner

Primary Examiner — Alvaro E Fortich
Assistant Examiner — Adam S Clarke
(74) Attorney, Agent, or Firm — WPAT, P.C

(57) ABSTRACT

Disclosed is an exploration method and system for pegmatite veins. The exploration method includes: three grounding electrodes are arranged at each observation point in a target area where pegmatite veins are located, and collecting electric field differences between two groups of grounding electrodes; drawing a multi-channel map, based on positions of the grounding electrodes, according to the electric field differences; obtaining resistivity variation characteristics of pegmatite veins according to the transverse variation of multi-channel map, and determining locations and lithologic characteristics of pegmatite veins according to the resistivity variation characteristics. Through functional modules with different functions, an exploration system is formed to realize the exploration method mentioned in the application.

1 Claim, 8 Drawing Sheets

EXPLORATION METHOD AND SYSTEM FOR PEGMATITE VEINS

CROSS-REFERENCE TO RELATED APPLICATIONS

This application claims priority to Chinese Patent Application No. 202111453224.4, filed on Dec. 1, 2021, the contents of which are hereby incorporated by reference.

TECHNICAL FIELD

The application relates to the exploration of pegmatite rare metals, and in particular to an exploration method and system for pegmatite veins.

BACKGROUND

Key mineral resources, such as lithium, beryllium are important metal raw materials in strategic emerging industries, such as new energy, new materials, information technology and other industries such as national defense and military industry, and are irreplaceable. Lithium and beryllium are important metal materials for China's "deep space exploration" and "clean energy industry", and the demand for lithium and beryllium resources will be multiplied in the coming 10-15 years. At present, as high as 80% of lithium and beryllium resources are imported. The currently exploited lithium-beryllium deposits in China are mainly of pegmatite type, and pegmatite type is a main type to achieve breakthrough in self-sufficiency of rare metals such as lithium and beryllium.

Although the main types of lithium-beryllium deposits are closely related to magmatic and hydrothermal activities, they are limited by the abundance of lithium-beryllium deposits. The exploration methods for lithium-beryllium deposits include spectral study, physical parameters and high-precision and high-resolution aerial magnetic survey technology, which can't directly explore the concealed pegmatite-type lithium-beryllium resources. Electromagnetic exploration is a main method to realize the exploration of metal minerals, but the conventional electromagnetic exploration is mostly an electromagnetic induction method. Although conventional electromagnetic exploration has strong abilities for detecting low-resistivity targets but great limitation for high-resistivity targets. Although an electric source electromagnetic method improves the resolution of high-resistivity targets to some extent by observing the electric field difference component, the electric source electromagnetic method is limited by a fact that the electromagnetic field excited by the source itself is generated by horizontal current, and is dominated by transverse electric field difference, and the detection capability in high resistivity targets is still limited. At the same time, the electric source electromagnetic method is insufficient in the resolution of a transverse variation of electrical structure, especially steeply inclined veinlets.

SUMMARY

In order to solve the existing technical problems, the application provides an exploration method for pegmatite veins, including:

setting three grounding electrodes at each observation point in a target area where pegmatite veins are located, and collecting electric field differences between two grounding electrodes;

drawing a multi-channel map, based on positions where the grounding electrodes are set, according to the electric field differences; and obtaining resistivity variation characteristics of the pegmatite veins according to a transverse change of multi-channel map, and determining locations and lithologic characteristics of the pegmatite veins according to the resistivity variation characteristics.

Optionally, drawing the multi-channel map includes following steps: in a process of collecting the electric field differences between two grounding electrodes, arranging the three grounding electrodes with a first distance, a second distance and a third distance, where a sum of the first distance and the second distance is equal to the third distance;

collecting a first electric field difference of the first distance and a second electric field difference of the second distance, and drawing the multi-channel map according to the third distance.

Optionally, drawing the multi-channel map includes following steps:

in the process of collecting the electric field differences between two groups of grounding electrodes, arranging the three grounding electrodes with the first distance, the second distance and the third distance, where the sum of the first distance and the second distance is greater than the third distance;

collecting the first electric field difference of the first distance and the second electric field difference of the second distance, and drawing the multi-channel map according to the first distance and the second distance.

Optionally, in a process of drawing the multi-channel map, the first distance and the second distance include a first included angle.

An included angle range of the first included angle is 60°-160°.

The first electric field difference of the first distance and the second electric field difference of the second distance are collected, and the multi-channel map is drawn according to the first distance and the second distance.

Optionally, in the process of drawing the multi-channel map, the first distance and the second distance include a second included angle.

The second included angle is greater than 0° and less than 60°.

A sum of projections of the first electric field difference and the second electric field difference on the third distance is obtained based on the second included angle, and the multi-channel map is drawn according to the first distance and the second distance.

Optionally, in the process of drawing the multi-channel map, the first distance and the second distance include a third included angle.

The third included angle is greater than 160° and less than 180°.

The multi-channel map is drawn according to the third distance and a sum of the first electric field difference and the second electric field difference.

The application also discloses an exploration system for pegmatite veins, including:

a data acquisition module used for setting three grounding electrodes at each observation point in a target area where pegmatite veins are located, and collecting electric field differences between two groups of grounding electrodes;

a data processing module used for drawing a multi-channel map, based on positions where grounding electrodes are set, according to the electric field differences;

a data analysis module used for obtaining resistivity variation characteristics of pegmatite veins according to a transverse change of the multi-channel map, and determining locations and lithologic characteristics of pegmatite veins according to the resistivity variation characteristics;

a display module used to display the target area, the multi-channel map, positions and the lithologic characteristics of the pegmatite veins.

Optionally, the data processing module is used to execute steps for drawing the multi-channel map.

The application discloses the following technical effects.

Considering that pegmatite veins have the characteristics of high resistivity, veinlets and steeply inclined distribution, the application proposes an exploration method for pegmatite veins. The exploration method for pegmatite veins makes use of the relatively high resolution of electric field differences of electric source transient electromagnetic to high resistivity, and innovatively proposes to observe the electric field differences of adjacent observation points, eliminate the influence of background electrical structure, strengthen the transverse variation of electrical structure, realize the precise detection of steeply inclined pegmatite veins, and overcome a problem of poor resolution of steeply inclined veins with high resistivity by a conventional observation mode of electric field differences between two observation points.

BRIEF DESCRIPTION OF THE DRAWINGS

In order to more clearly explain the embodiments of the present application or the technical schemes in the prior art, the following will briefly introduce the drawings that need to be used in the embodiments. Obviously, the drawings in the following description are only some embodiments of the present application. For those of ordinary skill in the art, other drawings can be obtained according to these drawings without any creative labor.

DETAILED DESCRIPTION OF THE EMBODIMENTS

Figure 1:
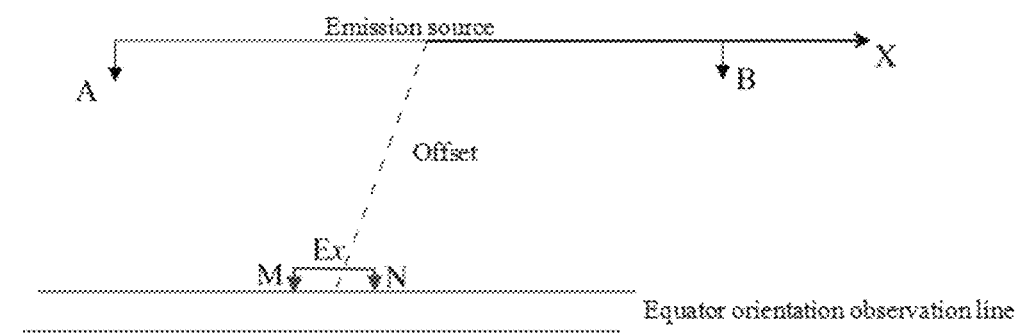
FIG. 1 is a conventional observation mode of electric field differences according to the present application.

In order to make the objectives, technical schemes and advantages of the embodiments of this application clearer, the technical schemes in the embodiment of this application will be clearly and completely described below with reference to the drawings in the embodiment of this application. Obviously, the described embodiment is only a part of the embodiment of this application, but not all the embodiments. Generally, the components of the embodiments of the present application described and illustrated in the drawings herein can be arranged and designed in various different configurations. Therefore, the following detailed description of the embodiments of this application provided in the drawings is not intended to limit the scope of the claimed application, but only to represent selected embodiments of this application. Based on the embodiments of this application, all other embodiments obtained by those skilled in the field without creative labor belong to the scope of protection of this application.

As shown in FIGS. 1-8, the present application provides an exploration method for pegmatite veins, including:

setting three grounding electrodes at each observation point in a target area where pegmatite veins are located, and collecting electric field differences between two groups of grounding electrodes;

drawing a multi-channel map, based on positions where the grounding electrodes are set, according to the electric field differences; and obtaining resistivity variation characteristics of the pegmatite veins according to a transverse change of multi-channel map, and determining locations and lithologic characteristics of the pegmatite veins according to the resistivity variation characteristics.

In an embodiment, drawing the multi-channel map includes following steps: in a process of collecting the electric field differences between two groups of grounding electrodes, arranging the three grounding electrodes with a first distance, a second distance and a third distance, where a sum of the first distance and the second distance is equal to the third distance;

collecting a first electric field difference of the first distance and a second electric field difference of the second distance, and drawing the multi-channel map according to the third distance.

In an embodiment, drawing the multi-channel map includes following steps:

in the process of collecting the electric field differences between two grounding electrodes, arranging the three grounding electrodes with the first distance, the second distance and the third distance, where the sum of the first distance and the second distance is greater than the third distance;

collecting the first electric field difference of the first distance and the second electric field difference of the second distance, and drawing the multi-channel map according to the first distance and the second distance.

In an embodiment, as for drawing the multi-channel map, in a process of drawing the multi-channel map, the first distance and the second distance include a first included angle.

An included angle range of the first included angle is 60°-160°.

The first electric field difference of the first distance and the second electric field difference of the second distance are collected, and the multi-channel map is drawn according to the first distance and the second distance.

In an embodiment, as for drawing the multi-channel map, in the process of drawing the multi-channel map, the first distance and the second distance include a second included angle.

The second included angle is greater than 0° and less than 60°.

A sum of projections of the first electric field difference and the second electric field difference on the third distance is obtained based on the second included angle, and the multi-channel map is drawn according to the first distance and the second distance.

In an embodiment, as for drawing the multi-channel map, in the process of drawing the multi-channel map, the first distance and the second distance include a third included angle.

The third included angle is greater than 160° and less than 180°.

The multi-channel map is drawn according to the third distance and a sum of the first electric field difference and the second electric field difference.

The application also discloses an exploration system for pegmatite veins, including:

a data acquisition module used for setting three grounding electrodes in a target area where pegmatite veins are located, and collecting electric field differences between two grounding electrodes;

a data processing module used for drawing a multi-channel map, based on positions where grounding electrodes are set, according to the electric field differences;

a data analysis module used for obtaining resistivity variation characteristics of pegmatite veins according to a transverse change of the multi-channel map, and determining locations and lithologic characteristics of pegmatite veins according to the resistivity variation characteristics;

a display module used to display the target area, the multi-channel map, positions and the lithologic characteristics of the pegmatite veins.

In an embodiment, the data processing module is used to execute steps for drawing the multi-channel map.

The application also includes setting more than three grounding electrodes, and every grounding electrode is arranged in a same straight line, and the electric field differences between every two electrodes are collected to draw the multi-channel map.

Embodiment 1

The conventional observation mode observes potential difference between MN (M refers to electrode M and N refers to electrode N) through two grounding electrodes MN. In other words, the electric field difference at a middle point of MN is observed. The electric field difference reflects the electrical characteristics of the electrical structures below and around this point, and is easily influenced by geological bodies other than below this point. Inversion results often cannot accurately reflect the electrical characteristics below this point, and the transverse resolution is also affected by a single point observation mode. At the same time, an observed transverse electric field difference Ex is mainly generated by horizontal current, mainly transverse electric field difference, which has limitations in the resolution of high resistivity targets.

The innovative observation mode is to observe the electric field differences by increasing the grounding electrode in the middle position and using $M_1$-N-$M_2$ three electrodes. The electric field differences at the middle point N are observed. Due to the smaller electrode distance, information of the underground electrical structure reflected by the electric field differences between $M_1N$ and $M_2N$ is effectively eliminated, variation characteristics of the horizontal electrical structure are enhanced, and more precise exploration of steeply incline veinlets is realized. At the same time, the proportion of transverse magnetic field included in the observed electric field differences is increased, and the transverse magnetic field has higher resolution than the transverse electric field difference. Based on these characteristics, the innovative mode realizes the precise exploration of steeply inclined pegmatite veins with high resistivity.

Taking the uniform earth as an example, the comparison results of the proportion of TM field in the transverse electric field difference of a same observation point and the electric field differences of adjacent points are as follows.

In the conventional observation mode, in the actual observed transverse electric field (TEM) difference, the TE field (except in a period of sign inversion) is stronger than the TM field, and the observed TEM field is dominated by TE field. However, in the innovative observation mode, TM is smaller than TE field except in a very short period of sign inversion (around 0.1 s), and TM field is larger than TE field at other times, and TM field is much larger than TE field after 10-3 s. The transverse electric field difference in the innovative observation mode mainly focuses on TM field. Using the advantages of strong detection ability of TM field to high resistivity targets can greatly improve the detection ability of electrical source transient electromagnetic to high resistivity targets.

Figure 2:
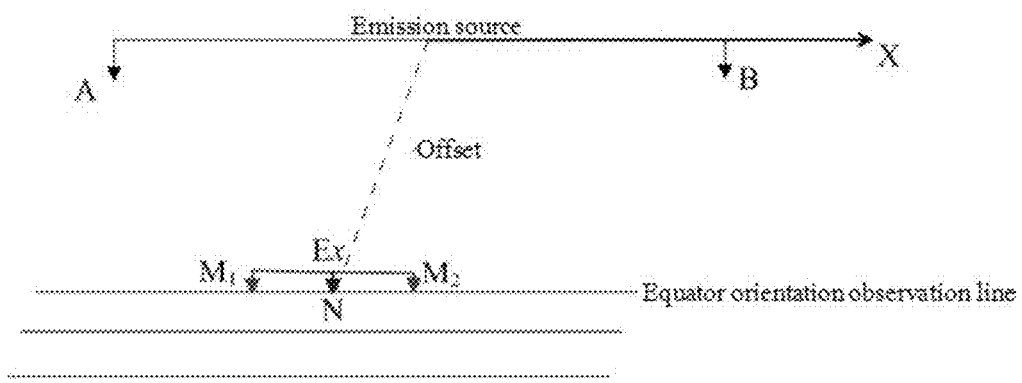
FIG. 2 is an innovative observation mode according to the present application.
Figure 3:
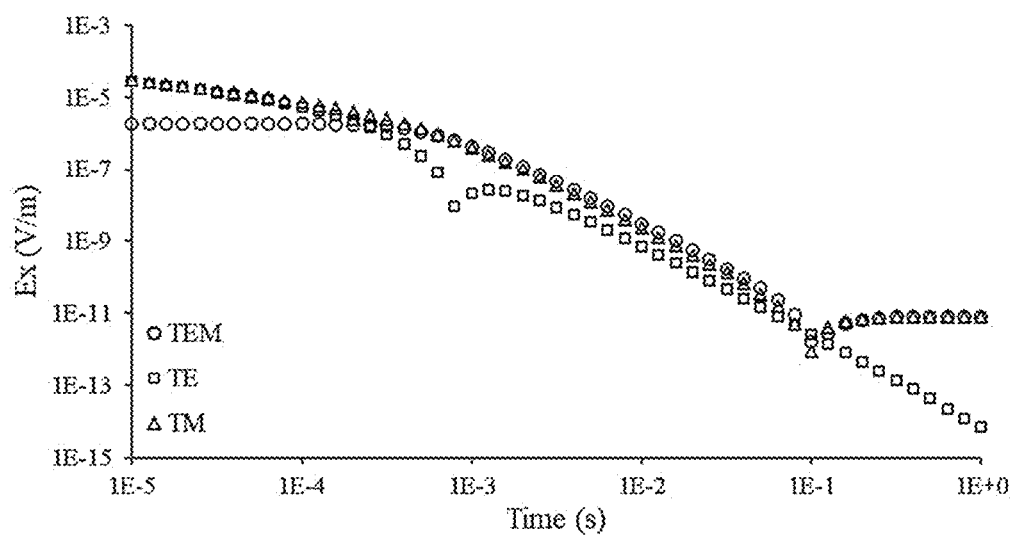
FIG. 3 shows a proportion of transverse electric (TE) field, transverse magnetic (TM) filed and transverse electric and magnetic (TEM) field between adjacent electric field differences according to the present application.
Figure 4:
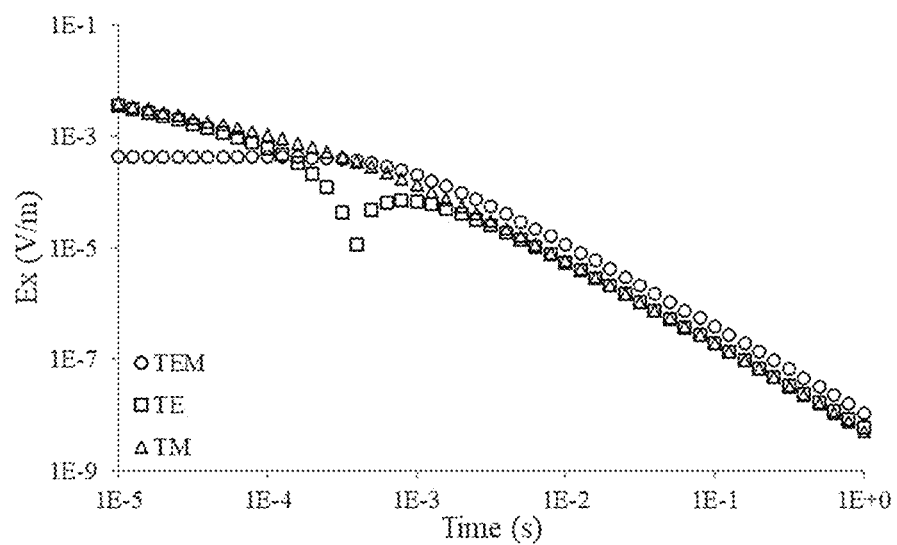
FIG. 4 shows a proportion of TE and TM in the conventional observation mode of the present application.

Specific steps: 1) during actual observation, adding another grounding electrode N in a middle of two conventionally used grounding electrodes $M_1$ and $M_2$ as shown in FIG. 2, simultaneously recording the electric field differences between these two pairs of electrodes ($M_1N$ and $M_2N$). $M_1$ and $M_2$ share one terminal on a receiving instrument, and N adopts another terminal. In this way, the electric field differences at N electrode are collected. For the conventional MN, the electric field differences at the middle point of MN are recorded. The electric field difference information includes the information below and around the observation point, while $M_1NM_2$ acquisition method reduces the earth surface information between adjacent points.

2) drawing the multi-channel map using the data obtained in a whole measuring line, and judging the resistivity variation characteristics of underground electrical targets according to the transverse variation of the multi-channel map curve and the increase or decrease of the transverse variation of numerical values.

3) obtaining resistivity variation characteristics of the pegmatite veins according to a transverse change of multi-channel map, and determining locations and lithologic characteristics of the pegmatite veins according to the resistivity variation characteristics.

Application example of exploring pegmatite type rare metal ore is as follows:

A mining area is generally distributed in the north-south-west-east direction, with an east-west length of 2,100 m, a north-south width of 200-400 m and an area of 0.48 km².

Through the method of the application, electrical parameters of various lithologies in the mining area are summarized, as shown in Table 1.

TABLE 1

| Lithology name | Sample | | H (%) | | | ρ (Ω·M) | | |
|---|---|---|---|---|---|---|---|---|
| | Piece count | Serial number | Maximum value | Minimum value | Average value | Maximum value | Minimum value | Average value |
| Marble | 19 | 201-219 | 1.93 | 0.24 | 0.77 | 8130 | 1573 | 5116 |
| Hornblende schist | 18 | 301-318 | 0.39 | 0.02 | 0.19 | 3250 | 713 | 1881 |
| Granitic pegmatite | 16 | 401-416 | 3.57 | 1.33 | 2.05 | 15312 | 4567 | 8613 |
| Quartz | 11 | 501-511 | 0.80 | 0.02 | 0.48 | 44425 | 9496 | 21972 |

From the statistics of lithology apparent resistivity in the above table: hornblende schist has the lowest apparent resistivity, marble has a higher apparent resistivity, granite pegmatite has a higher apparent resistivity, and Quartz vein has the highest apparent resistivity. These electrical differences provide reference basis for electrical parameters for classifying and identifying geophysical survey of strata (lithology) and structure.

Figure 5:
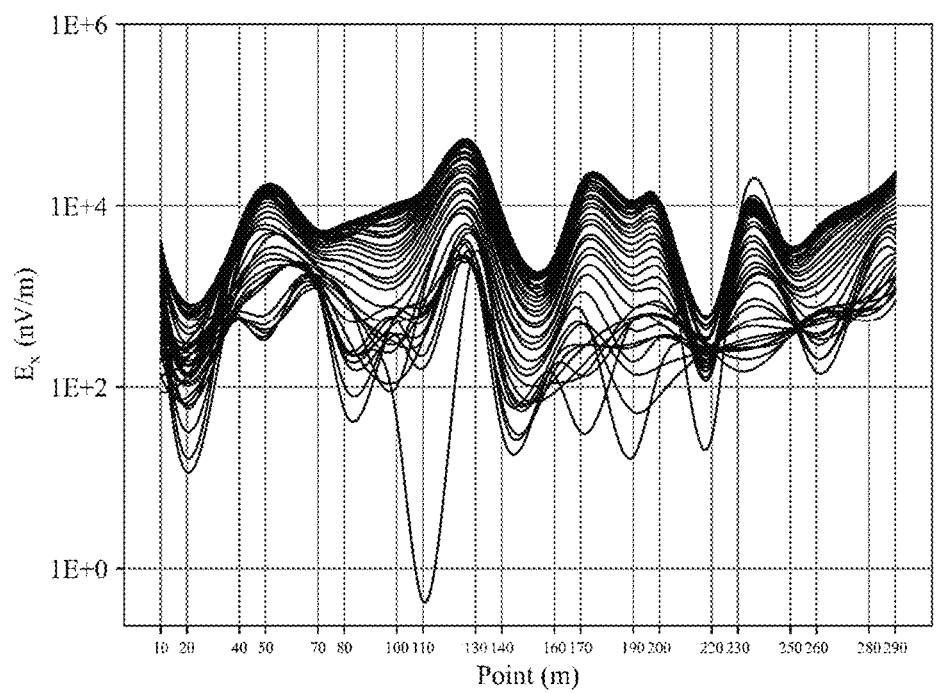
FIG. 5 is a profile of original data by an innovative observation mode according to the present application.
Figure 6:
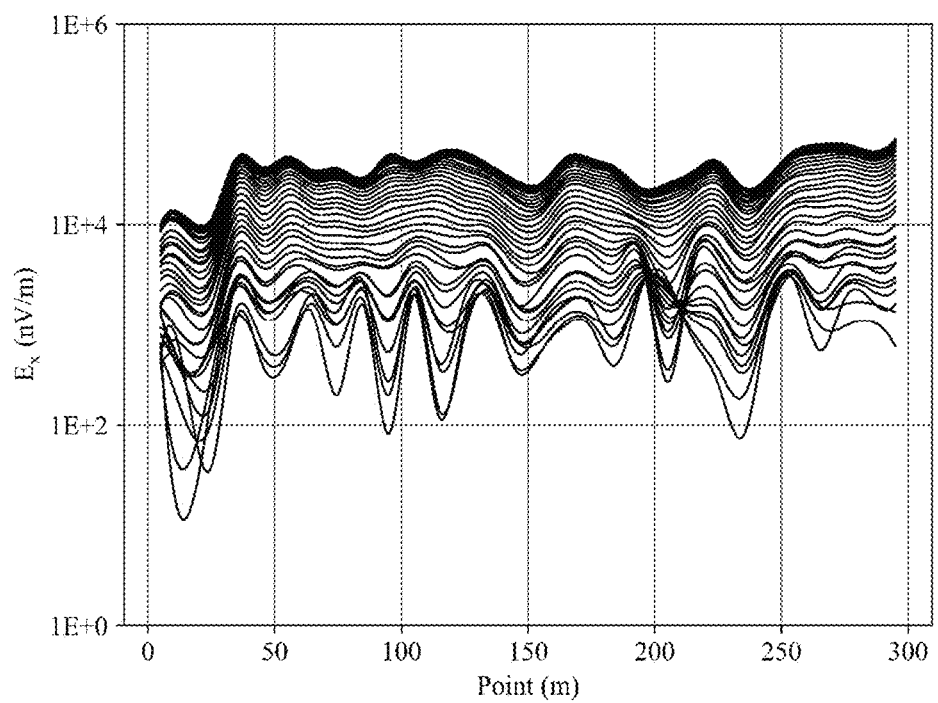
FIG. 6 is a profile of original data by a conventional observation mode according to the present application.
Figure 7:
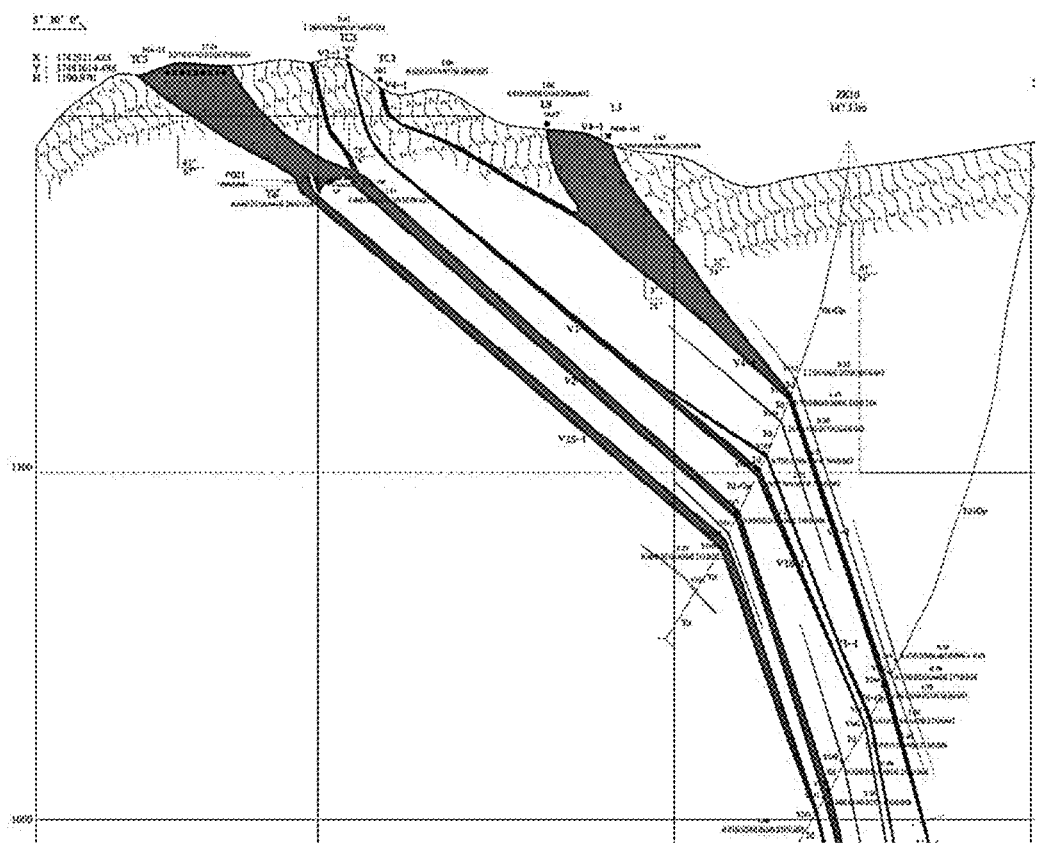
FIG. 7 is a cross-sectional view of verification according to the present application.
Figure 8:
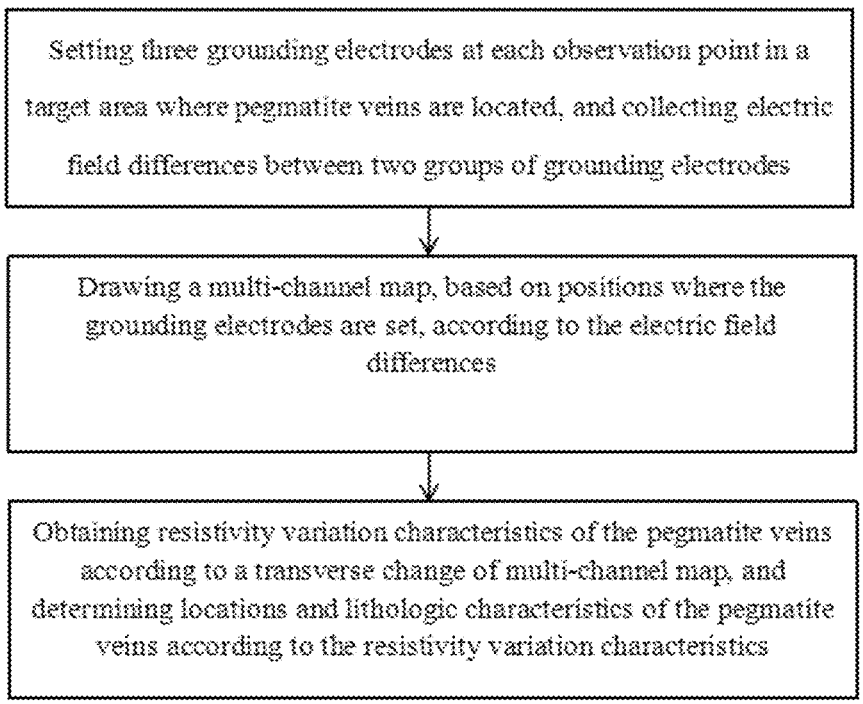
FIG. 8 is a schematic flow diagram of an exploration method for pegmatite veins according to the present application.

As shown in FIGS. 5-7, the observation results of the method have obvious variations in response characteristics in the observation points range of 30-45 and 130-150, which correspond to actual occurrence space of pegmatite veins. However, the conventional method increases a spatial area of this response characteristic due to volume effect, and reduces the transverse resolution.

It should be noted that similar symbols and letters indicate similar items in the following drawings, so once an item is defined in one drawing, it is not necessary to further define and explain it in the subsequent drawings. In addition, the terms "first", "second", "third" and so on are only used to distinguish descriptions, but not to indicate or imply relative importance.

Finally, it should be noted that the above-mentioned embodiments are only specific embodiments of the present application, which are used to illustrate the technical schemes of the present application, but not to limit it. Although the present application has been described in detail with reference to the above-mentioned embodiments, those skilled in the art should understand that any person familiar with the technical field can still modify or easily think of changes to the technical scheme described in the above-mentioned embodiments within the technical scope disclosed by the present application, or can equivalently replace some features of the technical scheme. These modifications, changes or substitutions do not make the essence of the corresponding technical solutions deviate from the spirit and scope of the technical solutions of the embodiments of the present application and should be included in the scope of protection of the present application. Therefore, the scope of protection of the present application should be based on the scope of protection of the claims.

What is claimed is:

1. An exploration method for pegmatite veins, comprising:
    setting three grounding electrodes at each observation point in a target area where pegmatite veins are located, and collecting electric field differences between two grounding electrodes;
    drawing a multi-channel map, based on positions where the grounding electrodes are set, according to the electric field differences; and
    obtaining resistivity variation characteristics of the pegmatite veins according to a transverse change of multi-channel map, and determining locations and lithologic characteristics of the pegmatite veins according to the resistivity variation characteristics;
    in a process of collecting the electric field differences between two grounding electrodes, the three grounding electrodes include a first distance, a second distance and a third distance;
    a sum of the first distance and the second distance is equal to the third distance;
    a first electric field difference of the first distance and a second electric field difference of the second distance are collected, and the multi-channel map is drawn according to the third distance;
    a sum of the first distance and the second distance is greater than the third distance;
    in a process of drawing the multi-channel map, the first distance and the second distance include a first included angle;
    an included angle range of the first included angle is 60°-160°;
    a first electric field difference of the first distance and a second electric field difference of the second distance are collected, and the multi-channel map is drawn according to the first distance and the second distance;
    in the process of drawing the multi-channel map, the first distance and the second distance include a second included angle;
    the second included angle is greater than 0° and less than 60°;
    a sum of projections of the first electric field difference and the second electric field difference on the third distance is obtained based on the second included angle, and the multi-channel map is drawn according to the first distance and the second distance;
    in the process of drawing the multi-channel map, the first distance and the second distance include a third included angle;
    the third included angle is greater than 160° and less than 180°; and
    the multi-channel map is drawn according to the third distance and a sum of the first electric field difference and the second electric field difference.

* * * * *